(12) United States Patent
Motoi

(10) Patent No.: US 7,297,947 B2
(45) Date of Patent: Nov. 20, 2007

(54) APPARATUS AND METHOD FOR EVALUATING CROSS SECTION OF SPECIMEN

(75) Inventor: Taiko Motoi, Atsugi (JP)

(73) Assignee: Canon Kabushiki Kaisha, Tokyo (JP)

(*) Notice: Subject to any disclaimer, the term of this patent is extended or adjusted under 35 U.S.C. 154(b) by 122 days.

(21) Appl. No.: 11/212,673

(22) Filed: Aug. 29, 2005

(65) Prior Publication Data

US 2006/0060777 A1    Mar. 23, 2006

(30) Foreign Application Priority Data

Sep. 7, 2004    (JP)    ............................. 2004-259826

(51) Int. Cl.
*G01N 23/00*    (2006.01)

(52) U.S. Cl. ...................... 250/306; 250/309; 250/307; 250/492.21; 250/491.1; 250/492.2; 250/492.3; 156/643; 156/662; 156/657; 437/38; 437/195; 437/189

(58) Field of Classification Search ................ 250/307, 250/309, 492.21, 491.1, 492.2, 492.3, 423 R, 250/370, 310, 306; 156/643, 662, 657; 437/195, 437/189; 257/429; 427/38
See application file for complete search history.

(56) References Cited

U.S. PATENT DOCUMENTS

| 4,516,253 | A | * | 5/1985 | Novak | ......................... 378/34 |
| 5,028,780 | A | * | 7/1991 | Kaito et al. | .................. 250/307 |
| 5,155,093 | A | | 10/1992 | Den et al. | |
| 5,504,340 | A | | 4/1996 | Mizumura et al. | |
| 5,633,502 | A | * | 5/1997 | Fischione | ............... 250/441.11 |
| 6,593,583 | B2 | * | 7/2003 | Iwasaki | ................... 250/492.1 |
| 6,727,500 | B1 | * | 4/2004 | Berger et al. | ............... 250/306 |
| 6,949,756 | B2 | * | 9/2005 | Gerlach et al. | ......... 250/492.21 |
| 2006/0197017 | A1 | | 9/2006 | Motoi et al. | |

FOREIGN PATENT DOCUMENTS

WO    03/032360    4/2003

* cited by examiner

Primary Examiner—Jack I. Berman
Assistant Examiner—Andrew Smyth
(74) Attorney, Agent, or Firm—Fitzpatrick, Cella, Harper & Scinto

(57) ABSTRACT

An apparatus for evaluating a cross section of a specimen in a specimen chamber, wherein the apparatus includes a specimen stage for placing the specimen, a temperature regulation unit for regulating the temperature of the specimen, an ion beam generation unit for irradiating the specimen with an ion beam thereby performing cross section processing and observation of the specimen, a detection unit for detecting emission signals emitted from the specimen in response to the irradiation of the ion beam for observing the specimen, and a marking unit for marking the specimen.

7 Claims, 5 Drawing Sheets

APPARATUS AND METHOD FOR EVALUATING CROSS SECTION OF SPECIMEN

BACKGROUND OF THE INVENTION

1. Field of the Invention

The present invention relates to an evaluating apparatus for acquiring information on a specimen, and more particularly to a cross section evaluating apparatus and a cross section evaluating method for processing and evaluating a cross section of a specimen of which state and shape vary according to a change in temperature.

2. Related Background Art

The demand for evaluation of a cross section or processing of a fine structure in organic materials, including bio-origin materials and plastics, is increasing together with the recent increase of functional devices.

As the principal methods of preparing a cross section, utilized for obtaining information on the structure of an organic material, there are known for example a cutting method with a blade, an embedding method in resin, an embedding method by freezing, a breaking method by freezing, an ion etching method etc., but, in case of observing the internal structure of an organic material with an optical microscope, there is usually adopted a method of embedding the organic material in a resin and cutting it with a microtome.

However, the observation with an optical microscope is limited to a macroscopic analysis of the cross section, and, since the cut-out position cannot be designated, a large amount of work has been necessary in repeating the cross-section preparing operation, in order to achieve observation and analysis of the structure of the designated position.

For this reason, there has recently been developed an FIB (Focused Ion Beam) apparatus as described in U.S. Pat. No. 5,504,340 by which a desired position can be processed. The FIB apparatus irradiates a specimen to be processed with a finely focused ion beam from an ion source, thereby achieving a processing operation such as etching. The etching technology with such an FIB apparatus is becoming more and more popular, and is currently widely utilized for a structural analysis and a defect analysis of a semiconductor material or the like, and for preparing a specimen for a transmission electron microscope.

However, in case the aforementioned conventional FIB apparatus is used for observation and analysis of the cross-sectional structure of a specimen of which the state or shape changes with the temperature, such as an organic material, the heat generated in the course of FIB processing causes a change in the temperature of the specimen, thereby varying the state or shape thereof, whereby the cross-sectional structure of the specimen cannot be exactly analyzed.

In consideration of the foregoing, WO03/032360A1 discloses an apparatus for evaluating the specimen using an FIB apparatus provided with means for maintaining a constant temperature of the specimen.

However, there is room for further improvement even in the evaluating apparatus disclosed in WO03/032360A1 from viewpoints of facilitating the evaluation of the specimen and enabling effective evaluation.

SUMMARY OF THE INVENTION

An object of the present invention is to provide an evaluating apparatus attained by further improving the evaluating apparatus disclosed in WO03/032360A1.

The apparatus for evaluating a cross section of a specimen provided by the present invention is an apparatus for evaluating a cross section of a specimen in a specimen chamber wherein the apparatus comprises a specimen stage for placing the specimen, temperature regulation means for regulating the temperature of the specimen, ion beam generation means for irradiating the specimen with an ion beam thereby performing cross section processing and observation of the specimen, detection means for detecting emission signals emitted from the specimen in response to the irradiation of the ion beam for observing the specimen and marking means for marking the specimen.

The method for evaluating a cross section of a specimen provided by the present invention comprises the first step in which the temperature of the specimen is regulated, the second step in which a predetermined part of the specimen is marked, the third step in which the part to be processed in the cross section of the predetermined part is confirmed by using the mark as an index, the fourth step in which the predetermined part is irradiated with an ion beam to cut out a cross section, the fifth step in which emission signals emitted from the specimen in response to the irradiation of the ion beam for observing the specimen are detected and the sixth step in which image information is acquired based on the detected signals.

According to the present invention, marking on the specimen is enabled and identification of the part to be processed and evaluated are facilitated, and thereby evaluation of the specimen can be efficiently performed.

In addition, according to the present invention, exposure i.e. cross section processing of a section for which the image information is desired is enabled and exact image information of a section for which the image information is desired can be acquired while the specimen in which temperature change may cause changes in the state or shape is regulated at a desired temperature. The temperature of the specimen is maintained at a desired temperature even in the course of marking and FIB processing and is therefore changes in the state or shape of the specimen are not resulted.

DESCRIPTION OF THE PREFERRED EMBODIMENTS

Figure 1:
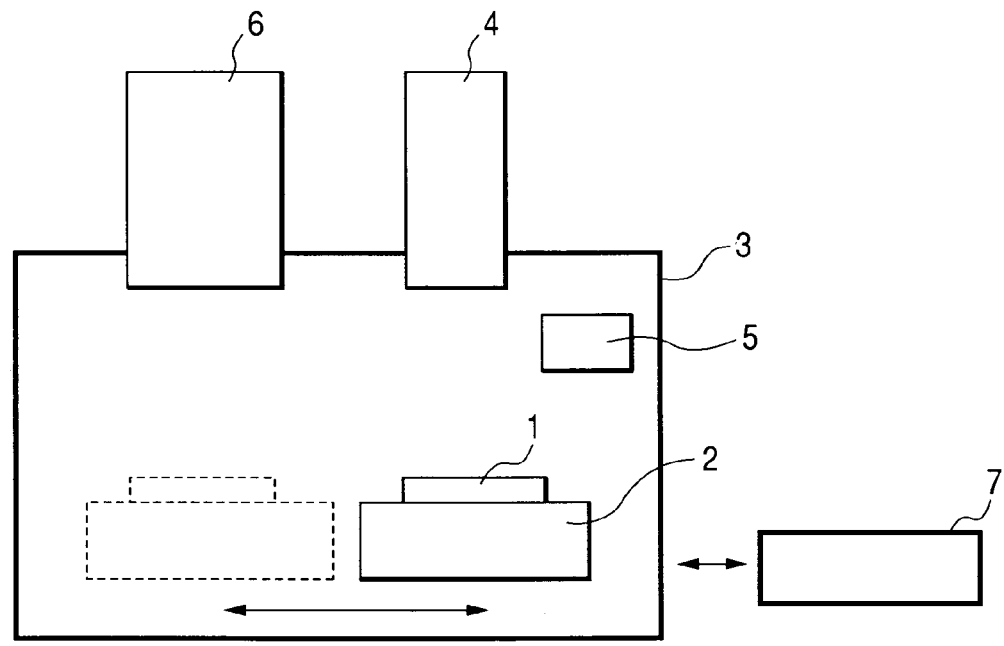
FIG. 1 is a view schematically showing the configuration of a cross section evaluating apparatus of the present invention in its first embodiment.

Embodiments of the present invention are described referring to the drawings.

The cross section in the present invention means not only a surface viewed from a section inside the specimen but also a surface observable from a certain point of view after the specimen is subjected to processing (including deposition and etching).

Embodiment 1

FIG. 1 is a view schematically showing the configuration of an apparatus for evaluating cross section of a specimen according to the first embodiment of the present invention.

The cross section evaluating apparatus is a focused ion beam apparatus for processing the cross section and it is provided with a heat retaining unit 2, on which a specimen 1 is fixed and which maintains the temperature of the specimen at a predetermined temperature. Heat retaining unit 2 can be accommodated in a specimen chamber 3.

Specimen chamber 3 is provided with an ion beam generation unit 4 for irradiating specimen 1 fixed to heat retaining unit 2 with an ion beam, and a detector 5 for detecting signals emitted from specimen 1 by the irradiation with the ion beam and also with marking means 6. The interior of specimen chamber 3 can be evacuated by a pump not shown in the figure to hold a predetermined low pressure, whereby the irradiation with the ion beam is rendered possible. In the present invention, the interior of the specimen chamber is preferably maintained at a pressure not more than 1E–2 Pa.

Ion beam generation unit 4 is used for irradiating specimen 1 with the ion beam thereby cutting out a cross section, and it can also be used for SIM (Scanning Ion Microscope) observation. In case of SIM observation, secondary electrons or secondary ions generated when specimen 1 is irradiated with the ion beam are detected by electron detector 5, and an image is formed based on the detected signals from electron detector 5.

Marking means 6 is used for marking specimen 1. It provides specimen 1 on a movable heat retaining unit 2 with a mark that can be observed by an SIM, as needed. The position to be evaluated can be easily confirmed by performing marking near the position to be evaluated even when the position to be processed and evaluated is difficult to be identified in an SIM image.

The detected signals from detector 5 are supplied to a control unit 7, which executes imaging in the aforementioned SIM observation as well as imaging in SEM (scanning electron microscope) observation. For example, control unit 7 acquires image information from the detection signals supplied from detector 5, and forms an image by causing a display apparatus (not shown) to display such image information. In addition, control unit 7 controls the ion beam generation in ion beam generation unit 4 and controls the irradiation and scanning of the ion beam onto specimen 1. The beam scanning operation can be controlled in the beam side and/or in the stage side on which the specimen is fixed, but the control at the beam side is preferable in consideration of the scanning speed etc.

The configuration of ion beam generation unit and so on may be so constructed as disclosed in the above-mentioned U.S. Pat. No. 5,504,340.

(Configuration of Temperature Regulating Means)

Temperature regulating means in the present embodiment is means performing temperature regulation of the specimen placed on a specimen stage.

Figure 2:
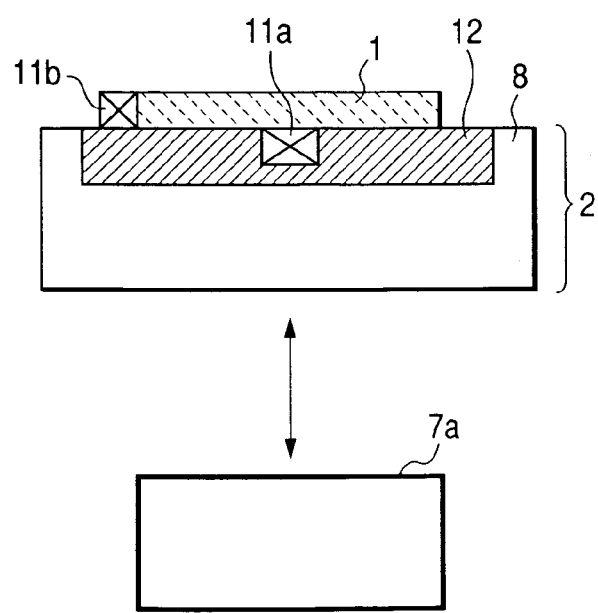
FIG. 2 is a view schematically showing the configuration of a temperature regulation means constituting a cross section evaluating apparatus of the present invention in its first embodiment.

FIG. 2 is a view schematically showing the configuration of a temperature regulation means constituting a cross section evaluating apparatus of the present invention in its first embodiment.

The temperature regulating means is comprised of a temperature varying mechanism which is attached to the specimen stage and on which the specimen is fixed, a first temperature detection means which is attached to a part of the temperature varying mechanism and detects the temperature in the vicinity of the specimen and temperature controlling means which regulates the temperature of the temperature varying mechanism based on the temperature detected by the first temperature detection means and maintains the specimen at a predetermined temperature and the temperature regulating means has a second temperature detection means which directly detects the temperature of the specimen.

Referring to FIG. 2, the temperature regulating means is comprised of a specimen stage 8 having a temperature varying mechanism 12 in a portion where specimen 1 is fixed, a thermometer 11a (first temperature detection means) which is attached to a part of temperature varying mechanism 12 and detects the temperature in the vicinity of specimen 1 fixed on temperature varying mechanism 12, temperature controlling means 7a which regulates the temperature of the temperature varying mechanism 12 based on the temperature detected by thermometer 11a and maintains specimen 1 at a predetermined temperature and a thermometer 11b which directly detects the temperature of specimen 1 (second temperature detection means). Temperature varying mechanism 12 and specimen stage 8 constitutes a heat retaining unit 2.

Although not shown in FIG. 2, there is also provided a display unit for displaying the temperature detected by thermometer 11b, whereby the operator can confirm the temperature of specimen 1, based on the temperature displayed on the display unit.

Temperature control unit 7a, which is part of the control unit 7 outside the specimen chamber 3, may also be constructed so as to regulate the temperature in temperature varying mechanism 12 based on the temperatures detected by both the thermometers 11a and 11b, thereby controlling the temperature of specimen 1 in more precise manner. Temperature control may be performed by using only thermometer 11b.

As described above, temperature controlling means regulate the temperature in temperature varying mechanism 12 based on the temperature detected by at least one of the first and second temperature detection means and maintains the specimen at a predetermined temperature.

Temperature varying mechanism 12 is constructed as a unit together with thermometer 11a, whereby a unit capable of controlling in a required temperature range can be installed in specimen stage 8. Such unit can be, for example, a high temperature unit having a heating mechanism such as a heater, or a low temperature unit having a cooling mechanism. Also, if necessary, there may be used a unit provided with a temperature varying function in both lower and higher temperature ranges than room temperature.

Specimen stage 8 is capable of moving and inclining in a predetermined direction and mechanically moving and inclining specimen 1 in the vertical or horizontal direction, thereby shifting specimen 1 to a desired position of evaluation. The movement control of specimen 1 by specimen stage 8 is conducted by the aforementioned control unit 7.

The aforementioned cooling mechanism can be a cooling mechanism such as a Peltiert element or a helium freezing device. Otherwise there may be adopted a system of providing a coolant pipe for flowing a cooling medium in a side of the heat retaining unit opposed to the specimen fixing portion to maintain a cooling medium such as liquid or vaporized nitrogen and water in thermal contact with the heat retaining unit.

Also in order to increase the absorption efficiency for the heat generated in the course of processing, there is preferably adopted a measure for improving the contact efficiency between the specimen and the cooling unit (heat retaining unit).

Such measure can be, for example, attained by preparing a specimen holder which is so constructed as to wrap around the specimen but not to interrupt the optical system of the apparatus to be used in the processing and observing operations, or by processing the specimen in a shape matching the shape of the stage and supporting the specimen with a maximum contact area on the stage.

It is also possible to provide a cooling member which further covers only a non-processed area of the specimen so as not to interrupt the beam system.

(Evaluating Method for Cross Section of Specimen)

In the following there will be explained a cross section evaluating method of the present invention.

Figure 3:
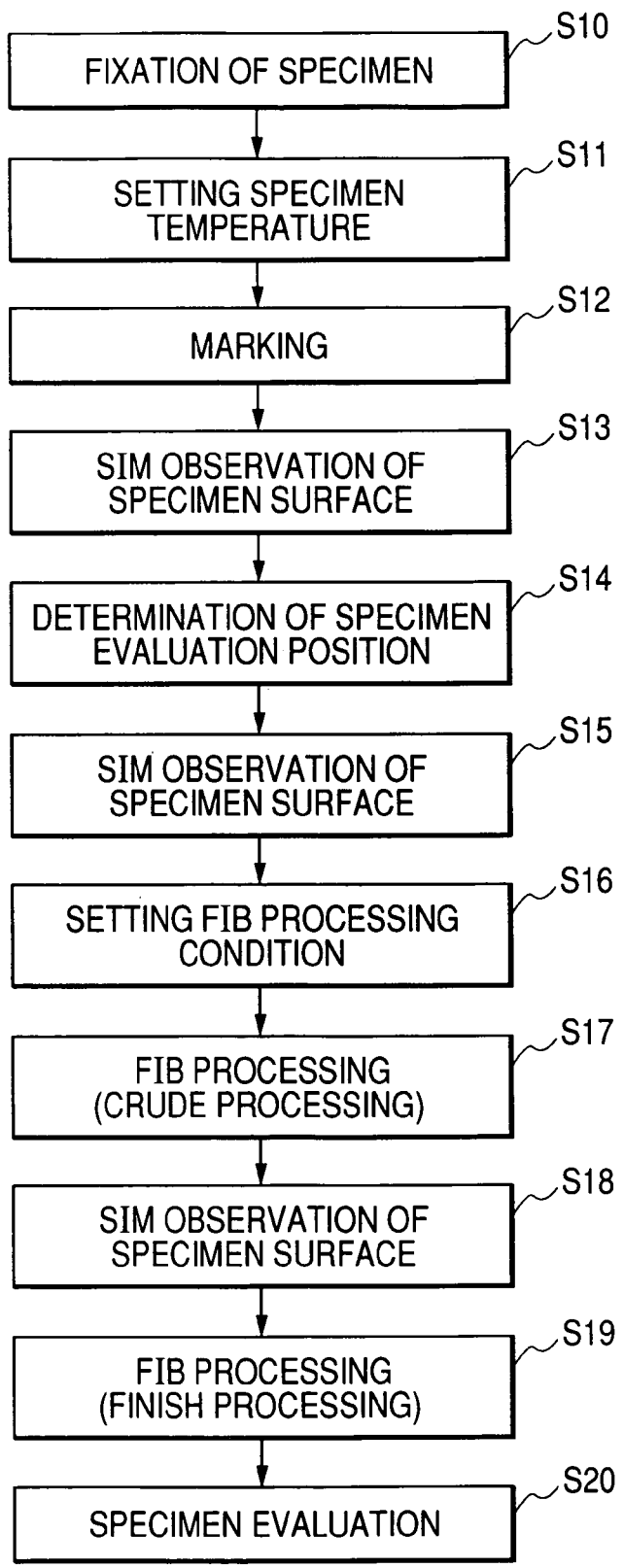
FIG. 3 is a flow chart showing a procedure of evaluating a cross section of a specimen using a cross section evaluating apparatus shown in FIGS. 1 and 2.

FIG. 3 is a flow chart showing a procedure of evaluating a cross section of a specimen using a cross section evaluating apparatus shown in FIGS. 1 and 2.

In the following there will be given an explanation on the procedure of cross sectional observation, with reference to FIG. 3, together with a detailed explanation on the control for the SIM observation by control unit 7 and on the temperature control on the specimen by temperature control unit 7a with such procedure.

At first, specimen 1 is fixed on a predetermined position (temperature varying mechanism 12) of specimen stage 8 (step S10) and inserted in specimen chamber 3, and an evaluation temperature is set (step S11). In response to the setting of the evaluation temperature, temperature control unit 7a controls temperature in temperature varying mechanism 12 whereby the temperature of specimen 1 is maintained at the set evaluation temperature.

In this state, the temperature of specimen 1 is detected by thermometer 11b, and the operator can confirm whether specimen 1 is maintained at the evaluation temperature based on the detected temperature displayed on the display unit (not shown).

In the present embodiment, it is preferable to effect the processing in a state where the specimen is cooled lower than room temperature. Also a cooling to not higher than 0° C. is more preferable because the specimen can be solidified if it contains moisture.

In such a cooling process, it is preferred to cool at first the specimen to a predetermined temperature not higher than room temperature, then hold the specimen in a reduced pressure and execute a processing operation by the irradiation of a focused beam while absorbing the heat generated from the vicinity of the irradiated portion of the specimen to retain the shape of the non-irradiated portion.

The cooling of the specimen may also be achieved by rapid cooling from room temperature. In this case, a cooling rate of 40° C./min or more is preferred. This method makes it possible to observe the cross section of a mixture in a rapidly cooled state when it is to be measured, where the dispersion of the mixture varies depending on the temperature.

The cooling step is preferably executed before the pressure reducing step, thereby making it possible to suppress the evaporation of the specimen caused by the reduced pressure. However, if the specimen consists of a substance showing little evaporation, the cooling may be executed simultaneously with the pressure reduction.

The cooling depends on the specimen to be processed. In case of an ordinary organic material such as PET, it is preferably cooled to a temperature range of 0 to −200° C., preferably −50° C. to −100° C.

Also if the processing time or the cooling time becomes excessively long at the cooling to the low temperature, a remaining gas in the specimen chamber or the substance generated at the processing may be adsorbed in the specimen of low temperature, thereby eventually hindering the desired processing or observation. It is therefore preferable to provide trap means for absorbing the remaining gas or the substance generated at the processing operation and to execute the processing or the acquisition of information while cooling such trap means.

The method of the present invention is advantageously applicable in case the object specimen is an organic material, particularly a material susceptible to heat such as a protein or other biological substances, or a moisture-containing composition. It is particularly preferable for a composition containing moisture, since the processing can be executed while the moisture is retained in the specimen.

In particular, the irradiation with the focused ion beam is executed under a reduced pressure. Therefore, in case of processing on a composition containing moisture or organic molecules with high volatility, there may result evaporation of moisture or such molecules by the heat generated in the course of the processing operation, and the presence of the temperature regulating means of the present invention is highly effective. It is also preferable, in order to achieve more exact processing and structural evaluation, to provide a step of determining in advance an appropriate temperature to be maintained at the processing. Such preferred temperature to be maintained can be determined by employing a specimen equivalent to the specimen to be processed, as a reference, executing the processing operation at plural temperatures and investigating the relationship between the damage in the processed portion and the cooling temperature.

After it is confirmed that specimen 1 has been maintained at an evaluation temperature, marking on the surface of specimen 1 is performed (step S12) while temperature of specimen 1 is always confirmed. This marking can be performed by moving specimen 1 to a marking position where it can be marked and a mark which is observable in an SIM image is formed in the vicinity of the position to be evaluated in the specimen while confirming with an optical microscope, a laser microscope and the like. Thus the position to be processed can be surely set in the SIM image by positioning relative to the mark even in a specimen where the position to be processed is difficult to be identified in the SIM image. Marking can be performed with a microscope and the like having a laser processing function.

It is possible to select a shape and position for the marking so that the position to be processed can be identified. On this occasion, marking can be suitably formed at a position identifiable and a recognizable shape by SIM image observation by which the position to be processed is determined. It is desirable to perform marking after the conditions not denaturing the position to be FIB processed are determined.

According to the present invention, since the marking can be performed while regulating the temperature of the specimen, a specimen which tends to be denatured and the like can be marked while the specimen is cooled or atmosphere therearound is controlled. In such a case, it is desirable to predetermine the temperature and the marking position depending on the material and shape of the specimen to be evaluated.

After marking, it is confirmed that the position to be FIB processed can be identified and then the stage is moved to FIB processing position and SIM observation of the surface of specimen 1 is performed (step S13). In the SIM observation, control unit 7 controls the ion beam irradiation by ion beam generation unit 4 and the movement of specimen stage 8, whereby specimen 1 is scanned by the ion beam from ion beam generation unit 4. In synchronization with the scanning operation, detector 5 detects the secondary electrons (or secondary ions; hereinafter the same), and control unit 7 displays an SIM image, based on the detected signals of the secondary electrons, on the display unit (not shown). Thus, the operator can execute SIM observation of the surface of specimen 1. The SIM observation is performed with a weak ion beam for observation. The SIM image includes a position to be FIB processed and a marking preliminarily formed in the marking step.

Then the position at which the cross section is evaluated is determined from the image obtained by the SIM observation of the surface of specimen 1 (SIM image displayed in the above-mentioned display unit) (step S14). At this time, since the position to be processed can be identified with reference to the mark in the SIM image and thus the position to be processed can be determined precisely even in the case where the cross section evaluation position is difficult to be identified in the SIM image.

The cross section evaluation position thus determined is further subjected to SIM observation with a processing beam (step S15).

Then the FIB processing conditions are set (step S16). In this setting of the FIB processing conditions, a cut-out area and a cut-out position are determined on the SIM image obtained by the SIM observation of the surface in the step S15, and there are set the cross section processing conditions including an acceleration voltage, a beam current and a beam diameter. The cross section processing conditions include crude processing conditions and finish processing conditions, which are both set at this point. In the crude processing conditions, the beam diameter and the processing energy are larger than those in the finish processing conditions. The cut-out area and the cut-out position can be determined on the SIM image obtained with the observation beam in the foregoing step S13, but, in consideration of the precision, they are preferably determined on the SIM image obtained with the ion beam which is used in the actual processing.

After the FIB processing conditions are set, an FIB processing (crude processing) (step S17) is carried out. In the crude processing, control unit 7 controls the ion beam generation unit 4 according to the crude processing conditions set as explained in the foregoing, and also controls the movement of specimen stage 8 whereby the cut-out area and cut-out position determined in the step S16 is irradiated with the ion beam of an amount necessary for cutting.

After the crude processing, the surface of specimen 1 is subjected to SIM observation to confirm, on an image obtained by the SIM observation (SIM image), whether the processing has proceeded close to the desired position (step S18). In case the processing has not proceeded close to the desired position, the aforementioned steps S17 and S18 are repeated. The steps S17 and S18 are repeated also in case where the surface SIM image on the processed cross section is extremely coarse, but, in such a case, there is added for example an operation of gradually reducing the amount of ion beam. The SIM observation of the surface in the step S18 is similarly controlled as in the foregoing step S13.

After the confirmation that the crude processing has proceeded close to the desired position, there is executed an FIB processing (finish processing) (step S19). In the finish processing, control unit 7 controls the ion beam generation unit 4 according to the finish processing conditions set as explained in the foregoing, and also controls the movement of specimen stage 8 whereby the crude finished portion obtained in the step S17 is irradiated with the ion beam of an amount necessary for finish processing. Such finish processing provides a smooth cross section enabling the observation with a high magnification, for example, by an SEM.

As for the specimen thus completed with processing, the cross section is observed from the side and therefore the stage can be inclined with the temperature of the specimen maintained, thereby an SIM image can be obtained by scanning with a weak ion beam for observation and the form and state of the cross section at the processed position can be evaluated (step S20). In addition, if necessary, the temperature of the specimen can be allowed to return to room temperature and the specimen can be taken out and evaluated with another evaluating apparatus.

As explained in the foregoing, the cross sectional evaluation method of the present embodiment is capable of maintaining the evaluated specimen 1 always at the predetermined temperature, so that the state and morphology of specimen 1 do not change in the course of the FIB processing. Consequently the fine structural analysis can be achieved in precise manner.

Also in the embodiment explained above, ion beam processing does not generate shear stress, compression stress nor tension stress observed in machining such as cutting and polishing and therefore provides a sharp cross section for a composite specimen in which materials different in hardness and brittleness are mixed, a specimen having voids, a fine organic structure formed on the substrate, a specimen which can be easily dissolved in a solvent, and etc.

Further, the technique can maintain the temperature of the specimen at a predetermined value and therefore, the direct processing can be performed at a desirable predetermined temperature and at a designated position without breaking the layered structure even in the specimen containing a material whose state and morphology does change in accordance with the temperature.

The cross sectional evaluation method of the present embodiment described above is effective in analyzing a polymer structure on various substrates such as glass, microparticles, a polymer structure containing liquid crystal, a structure in which particles are distributed in a fibrous material and temperature transition material at a desired temperature. Furthermore, it is needless to say that the method is effective even for specimens susceptible to ion or electron beams.

In the foregoing embodiment of the present invention, a method for evaluating a cross section of a specimen has been described. The present invention, is, however, not limited to these. For example, a method for evaluating a surface of specimen by surface observation comprising removing substances attached on the surface to expose the surface to be observed is also included in the present invention.

Embodiment 2

Figure 4:
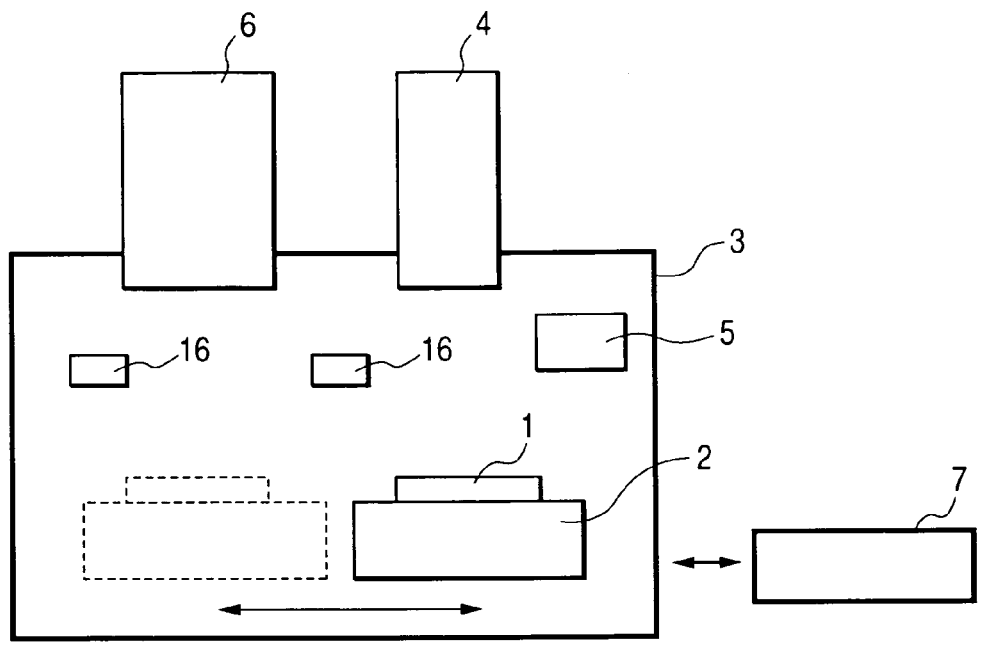
FIG. 4 is a view schematically showing the configuration of a cross section evaluating apparatus of the present invention in its second embodiment.

FIG. 4 is a view schematically showing the configuration of a cross section evaluating apparatus of the present invention in its second embodiment.

As shown in FIG. 4, the present embodiment is provided, in addition to the configuration of the embodiment 1, with trap means 16 for preventing re-deposition of the gas remaining in the specimen chamber or the substances generated at the processing operation, onto the specimen.

Such trap means 16 is composed for example of a material of high thermal conductivity such as a metal, and is maintained at a temperature equal to or lower than that of the specimen while it is cooled.

The present embodiment is effective, in case of processing or observation in a state of maintaining the specimen not higher than room temperature, in preventing the deposition of impurities onto the specimen.

Such trap means 16 is provided, in a state where the stage with the specimen supported thereon, the ion beam generation means, the electron beam generation means and the detection means are positioned, in such a position as not to hinder the beam systems in the detecting or processing operation. For improving the trapping efficiency, such trap means 16 is preferably positioned as close as possible to the specimen, as long as it does not hinder such detecting or processing operation. Also the trap means may be provided in more than one unit in the specimen chamber maintained at a low pressure.

Embodiment 3

Figure 5:
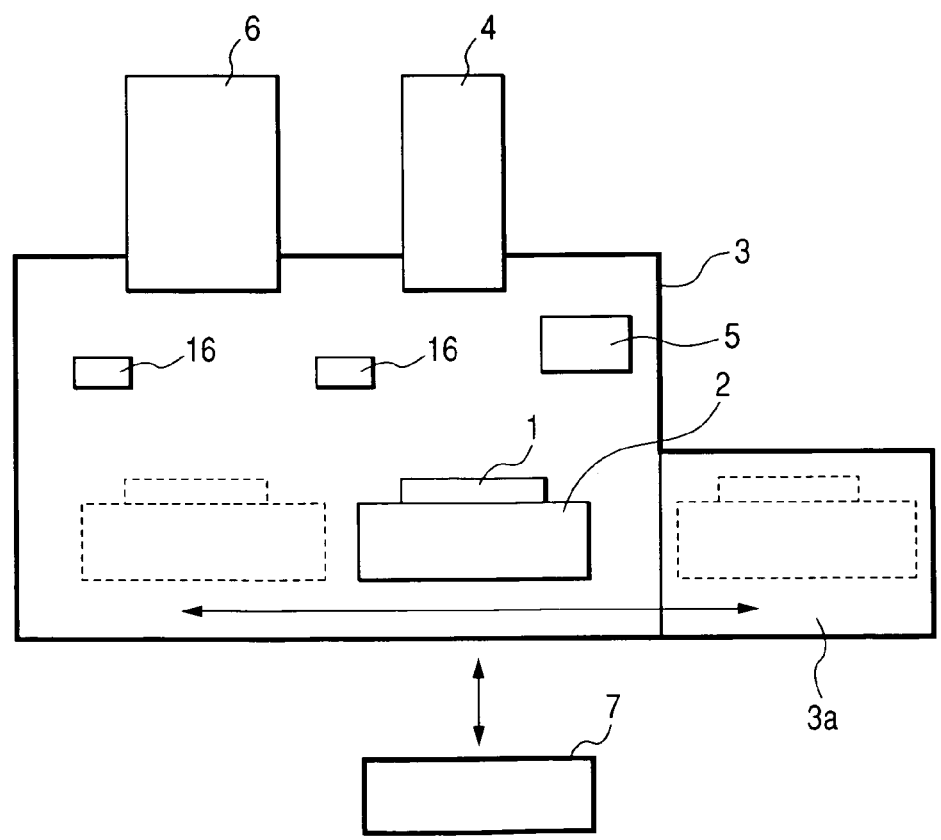
FIG. 5 is a view schematically showing the configuration of a cross section evaluating apparatus of the present invention in its third embodiment.

FIG. 5 is a view schematically showing the configuration of a cross section evaluating apparatus of the present invention in its third embodiment;

In the present embodiment, as shown in FIG. 5, a configuration with the second specimen chamber separately positioned from the specimen chamber of the main body in which the processing of the specimen is shown. The specimen is processed in the first specimen chamber 3 of the main body and transferred to the second specimen chamber 3a while the vacuum is maintained and after the vacuum line between the first specimen chamber 3 and the vacuum line is separated, a dry gas can be introduced into the second specimen chamber 3a through a gas introducing unit (not shown). Thus the introduction of the gas does not affect the first specimen chamber 3 at all and enables a configuration in which the first specimen chamber 3 is formed as small as possible. The second specimen chamber 3a can be used as a preliminary specimen chamber prior to introducing a specimen into the first specimen chamber 3 of the main body, thereby providing a configuration enabling efficient introduction of specimen.

Embodiment 4

The present embodiment shows an example of applying the apparatus of the present invention as a cross section evaluating apparatus in a manufacturing process for a liquid crystal display device or an organic semiconductor device.

In the present embodiment, there will be explained a case of executing temperature regulation on the specimen of a relatively large area.

In case of exactly evaluating the cross sectional state in a part of a large-sized specimen, such as a glass substrate coated with liquid crystal and to be used in a large-size liquid crystal display device, it is preferable to regulate the temperature of the entire substrate, though a local temperature regulation of an area around the processed portion is also possible. In such a case, the entire holder may be cooled by providing a coolant pipe for circulating a cooling medium, in a position opposed to the specimen supporting surface of the heat retaining unit.

EXAMPLES

In the following there will be explained examples of cross sectional evaluation with the cross section evaluating apparatus of the foregoing embodiments.

The present example employed the cross sectional evaluation apparatus shown in FIG. 1. Heat retaining unit 2 consisted of a specimen stage 8 as shown in FIG. 2 coupled with a unit having a low-temperature varying mechanism, and there was executed a cross sectional evaluation of a specimen, prepared by forming a polymer structure containing liquid crystal (two-frequency drive liquid crystal DF01XX, manufactured by Chisso Co.) (structure being obtained by mixing and polymerizing synthesized monomers HEMA, R167 and HDDA with liquid crystal) on a glass substrate, in the following procedure.

First, the specimen was fixed with carbon paste on the unit provided with the low-temperature varying mechanism, and this unit was set on specimen stage 8. After specimen stage 8 with the specimen set thereof was introduced in specimen chamber 3, the interior thereof was evacuated to a predetermined low pressure.

Then the temperature was set at −100° C., and it was confirmed that the specimen was maintained at such evaluation temperature.

Figure 6A:
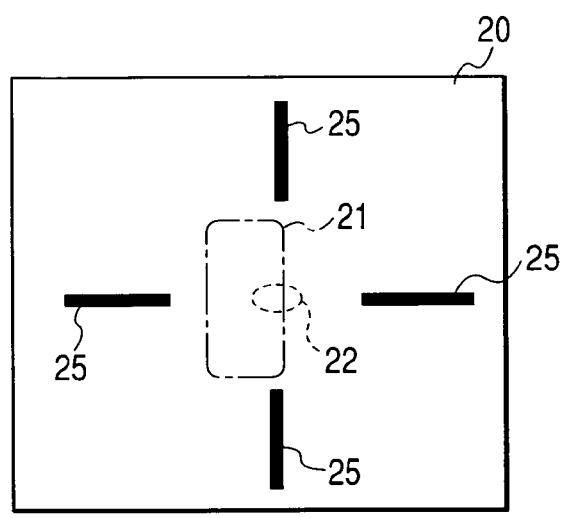
FIG. 6A is a schematic view of a microscopic image showing an example of a surface of a specimen after marking near the position to be evaluated.
Figure 6B:
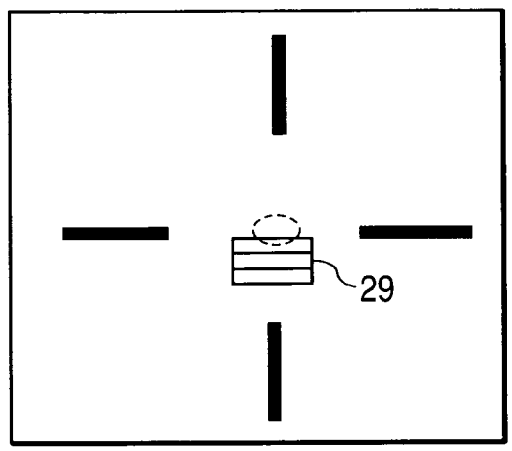
FIG. 6B is a schematic view of an SIM image at the same position as in FIG. 6A after the position to be evaluated is determined.
Figure 6C:
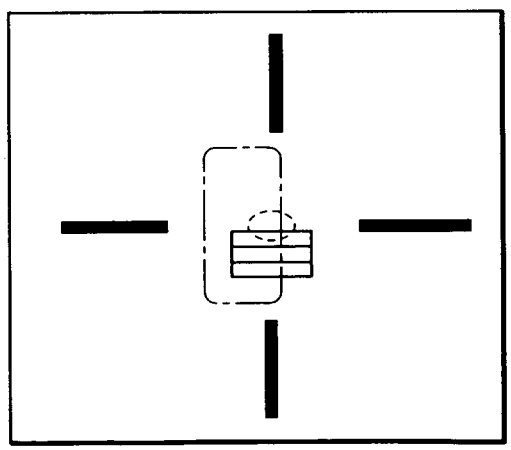
FIG. 6C is a schematic view showing a microscopic image after FIB processing.

FIG. 6A is a schematic view of a microscopic image showing an example of a surface of a specimen after marking near the position to be evaluated, FIG. 6B is a schematic view of an SIM image at the same position as in FIG. 6A after the position to be evaluated is determined and FIG. 6C is a schematic view showing a microscopic image after FIB processing.

The specimen stage was moved to a marking position and the surface of the specimen was observed with an equipped optical microscope and the position to be evaluated with an extraneous material on the line was confirmed. Four marks were formed in the vicinity of the position to be evaluated with a laser beam (FIG. 6A). The center of the surface of the specimen 20 had line 21 and the position to be evaluated 22. There are marks 25 on the upper, lower, right and left sides with a central focus on the position to be evaluated 22 and therefore it is a configuration enabling identification of the position to be evaluated based on these marks.

Then the specimen stage was moved to FIB processing position and the surface of the specimen was subjected to SIM observation for the region containing the cross section observing position while the temperature of the specimen was constantly checked. The ion beam used in this operation was made very weak in the observation mode. More specifically, there was employed a gallium ion source, with an acceleration voltage of 30 kV, a beam current of 20 pA and a beam diameter of about 30 nm. At this time, line 21 could not be recognized in the SIM image and the position to be evaluated 22 could be only faintly recognized, but FIB processing position 29 was set based on the four marks (FIG. 6B).

Then the designated cross section processing position was subjected to FIB processing (crude processing) More specifically, there were employed an acceleration voltage of 30 kV, a beam current of 50 nA and a beam diameter of about 300 nm to form a rectangular recess of a side of 40 μm and a depth of 30 μm in the cross section processing position. The crude processing was executed stepwise in small amounts under a weak condition, and the cross section of the specimen was often SIM observed in the course of processing, in order to confirm that the processing proceeds close to the desired position.

When the processing was almost completed, the specimen stage was moved to the marking position and the vicinity of the position to be evaluated was observed with an equipped optical microscope and it was confirmed that the position to be evaluated on the line 21 was FIB processed (FIG. 6C).

After confirmation that the processing proceeded to the desired position, the cross section processing position obtained by crude processing was further subjected to a finish processing for improving the precision of the cross section processing under a weak condition similar to that in the SIM observation but with a finer beam than in the crude processing.

Figure 7A:
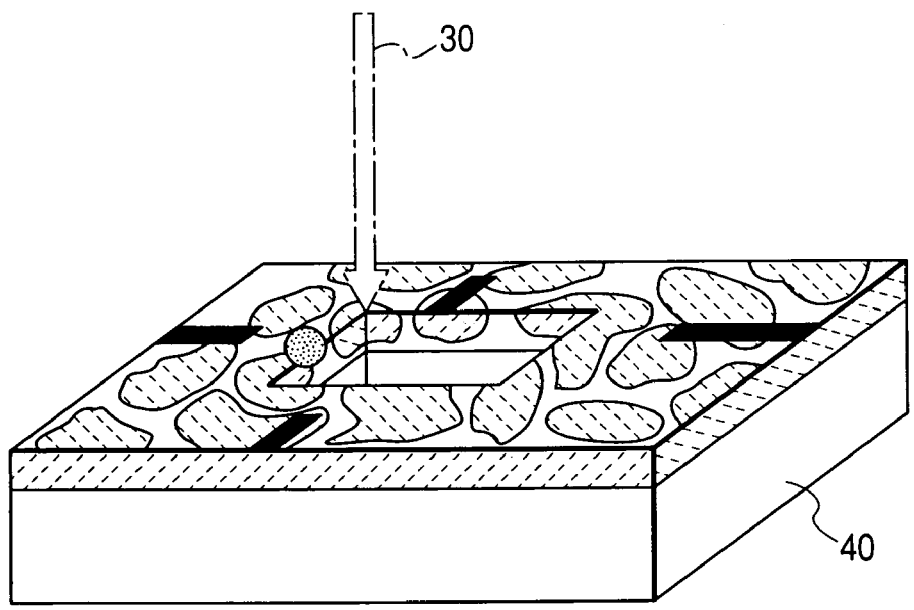
FIG. 7A is a schematic view showing an example of a cross section prepared by FIB processing.

FIG. 7A is a schematic view showing an example of a cross section prepared by FIB processing.

Figure 7B:
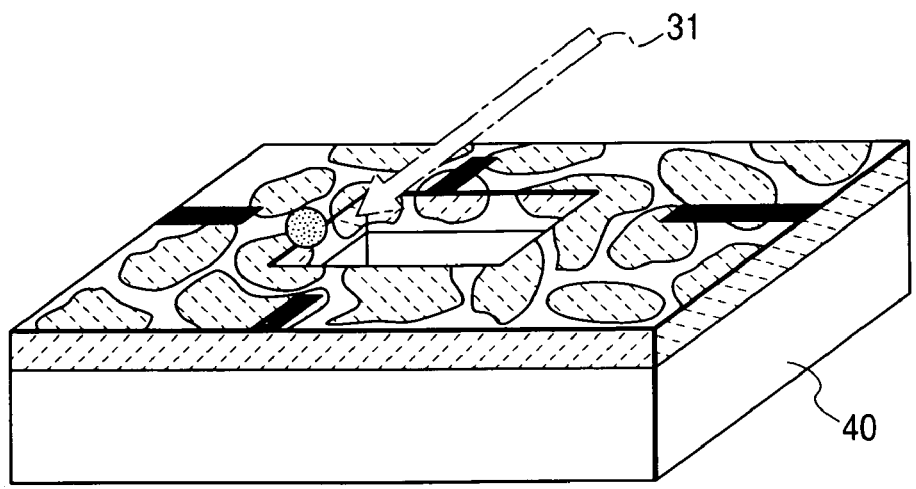
FIG. 7B is a schematic view showing a state of the cross section shown in FIG. 7A when observed by SIM.

FIG. 7B is a schematic view showing a state of the cross section shown in FIG. 7A when observed by SIM.

In FIG. 7A, a rectangular recess is formed by the irradiation of the ion beam 30 approximately at the center of the specimen 40. In the cross section SIM observation on the way, the stage was inclined and a weak ion beam 31 for observation was irradiated at an angle shown in FIG. 7B to perform confirmation. In this way, the cross section of the specimen can be observed from the side.

Then the temperature of the specimen was slowly returned to room temperature in specimen chamber and after the pressure inside specimen chamber 3 was elevated with dry nitrogen from which water was sufficiently removed, specimen 1 was taken out of the FIB apparatus.

Finally, the cross section of the specimen thus prepared was subjected to an SEM observation. The SEM observation was made under the conditions of an acceleration voltage of 800 V and a magnification up to 50,000 times, and demonstrated the liquid crystal enclosed in the polymer layer.

In this example, the cross section could be processed without deformation of the liquid crystal layer in the course of processing, since the FIB processing was executed while the specimen was maintained at −100° C. The shape of the cross section was confirmed by conducting SIM observation in an FIB apparatus. Further, the cross section showing the liquid crystal present in the polymer could be observed since it could be introduced to SEM and the SEM observation could be executed.

This application claims priority from Japanese Patent Application No. 2004-259826 filed Sep. 7, 2003, which is hereby incorporated by reference herein.

What is claimed is:

1. An apparatus for evaluating a cross section of a specimen in a specimen chamber, wherein the apparatus comprises:

a specimen stage for placing the specimen;

a temperature regulation unit for cooling the specimen to not higher than 0° C.;

an ion beam generation unit for irradiating the specimen with an ion beam thereby performing cross section processing and observation of the specimen;

a detection unit for detecting emission signals emitted from the specimen in response to the irradiation of the ion beam for observing the specimen; and a marking unit provided with a laser for marking the specimen.

2. The apparatus for evaluating a cross section of a specimen according to claim 1, wherein the apparatus further comprises:

an information acquiring unit for acquiring image information based on the detection of the signals by the detection unit.

3. The apparatus for evaluating a cross section of a specimen according to claim 1, wherein marking of the specimen by the marking unit, irradiation with an ion beam by the ion beam generation unit and detection of the emission signals by the detection unit are executed in a state where the specimen is maintained at a predetermined temperature by the temperature regulation unit.

4. The apparatus for evaluating a cross section of a specimen according to claim 1, wherein the specimen stage, the ion beam generation unit and the detection unit are provided in the specimen chamber of which the atmosphere is controllable, and the specimen chamber further contains a trap unit for capturing gas remaining therein.

5. The apparatus for evaluating a cross section of a specimen according to claim 1, wherein said specimen chamber is a first specimen chamber and the apparatus further comprises a second specimen chamber, of which the atmosphere is controllable, at such a position that the second chamber can communicate with the first chamber.

6. The apparatus for evaluating a cross section of a specimen according to claim 2, wherein the irradiation of the specimen with an ion beam for observation by the ion beam generation unit is executed by scanning a predetermined cross section before and after the processing and the information acquisition unit acquires an image information relating to the cross section based on emission signals from plural points thereof detected by the detection unit in synchronization with said scanning.

7. A method for evaluating a cross section of a specimen, wherein the method comprises:

a first step in which the temperature of the specimen is regulated to not higher than 0° C.;

a second step in which a predetermined part of the specimen is marked with a laser;

a third step in which a part to be processed in the cross section of the predetermined part is confirmed by using the mark as an index;

a fourth step in which the predetermined part is irradiated with an ion beam to cut out the cross section;

a fifth step in which emission signals emitted from the specimen in response to the irradiation of the ion beam for observing the specimen are detected; and a sixth step in which image information is acquired based on the detected signals.

* * * * *